(12) United States Patent
Sim (10) Patent No.: US 6,402,513 B1
(45) Date of Patent: Jun. 11, 2002

(54) DENTAL MODEL ARTICULATOR

(76) Inventor: Gordon K. Sim, 3390 De La Cruz Blvd., Suite L, Santan Clara, CA (US) 95054

( * ) Notice: Subject to any disclaimer, the term of this patent is extended or adjusted under 35 U.S.C. 154(b) by 0 days.

(21) Appl. No.: 09/730,965

(22) Filed: Dec. 7, 2000

(51) Int. Cl.$^7$ .......................... A61C 11/00; A61C 19/00
(52) U.S. Cl. ............................ 433/57; 433/34; 433/60; 433/74
(58) Field of Search .............................. 433/57, 58, 59, 433/60, 61, 62, 63, 64, 65, 66, 67, 55, 56, 54, 34, 74

(56) References Cited

U.S. PATENT DOCUMENTS

| | | | | |
|---|---|---|---|---|
| 2,094,903 A | * | 10/1937 | Pittman et al. | 433/56 |
| 2,911,722 A | * | 11/1959 | Benfield et al. | 433/60 |
| 3,823,476 A | * | 7/1974 | Hudson et al. | 433/54 |
| 4,207,677 A | * | 6/1980 | Lampert | 433/60 |
| 4,412,822 A | * | 11/1983 | Blechner | 433/60 |
| 4,451,234 A | * | 5/1984 | Oye | 433/54 |
| 5,046,949 A | * | 9/1991 | Richardson | 433/57 |
| 5,360,337 A | * | 11/1994 | Westdyk | 433/64 |
| 5,378,148 A | * | 1/1995 | Mogensen | 433/64 |
| 5,466,152 A | * | 11/1995 | Walter | 433/60 |
| 5,913,681 A | * | 6/1999 | Cho | 433/60 |

* cited by examiner

*Primary Examiner*—John J. Wilson (57) ABSTRACT

The articulator of the present invention provides relative manipulation of dental casts for simulation of occlusal and masticatory movements of the mouth. The articulator consists of three parts—a lower frame, an upper frame, and a middle frame. The lower frame is comprised of an elongated rectangular box, a bracket, and a male hinge. The elongated box has an open bottom and an insert at the top with a series of grooves. The upper frame is comprised of an elongated, channeled surface, a deformable bracket, a female hinge, and a platform with holes. The bottom surface has flat areas to attach a pre-prepared cast with an adhesive. Outside of the flat areas are two rectangular boxes to pour the model stone, forming the opposing cast. A platform with three holes is provided for maintaining the original vertical height of the jaws. The horizontal section of the bracket may be softened by heating for quick bite correction and remounting. The middle frame is snap-seated on top of the elongated box in the lower frame, forming a rectangular box which is filled with the model stone.

10 Claims, 6 Drawing Sheets

DENTAL MODEL ARTICULATOR

TECHNICAL FIELD

The present invention relates to dental prosthetics. More particularly, the invention relates to the method and structure for constructing dental models and for supporting the dental models in a manner which replicates normal mouth movements.

BACKGROUND OF THE INVENTION

Devices intended to support dental models are commonly known in the industry as dental model articulators. These devices have been used for a number of years to construct removable or fixed prosthetic appliances such as dentures, crowns and bridges.

The dental appliances are constructed and adjustments are made before insertion into the patient's mouth. For example, during construction of a crown, it is desirable to study the crown for compatibility with the patient's mouth and existing teeth. To accomplish this, the dental models are mounted on a device in a manner which enables the simulation of the patient's mouth during occlusal and masticatory movement.

Inexpensive disposable articulators currently in use are disclosed in U.S. Pat. Nos. 4,196.518, 4,382,787, 4,449,930, 4,533,323, 4,548,581, and 5,482,460. These articulators incorporate lockable ball-and-socket elements and flexible hinged brackets to mount the upper and lower dental models. When the correct bite relationship is found, the ball-and-socket joints are immobilized with an adhesive. The resiliently flexible bracket and hinge permit simulation of translatory movement, multi-axis pivotal movement, a full range of occlusal and masticatory movements, and other functions. Other U.S. Patents describing articulators include U.S. Pat. Nos. 3,466,750, 4,196,518 and 4,169,314.

However, these articulators, particularly the inexpensive ones, disclosed in U.S. Pat. Nos. 4,548,581 to Huffman and 5,482,460 to Farnor, Jr., have several deficiencies. Once the ball-and-socket joints are fixed with an adhesive, the models cannot be dismounted. Many times remounting is required since the bite record taken in the patient's mouth is often incorrect. When the mounting is incorrect, these articulators, which do not have any means of remounting, need to be forcefully detached from the models and then be replaced for remounting. This process is cumbersome and time consuming. Another deficiency is that these articulators do not provide a vertical stop. When many teeth are missing or there are no opposing teeth to come into contact with, the upper and lower models collapse. When mounting these kinds of models with articulators that do not have built-in vertical stops, external vertical stops need to be constructed during the impression-pouring process. Another deficiency is that these devices do not provide a self-cleaning mechanism, requiring extensive model trimming and grinding. Yet another deficiency is the numerous steps involved, requiring extensive model work.

SUMMARY OF THE INVENTION

The articulator of the present invention provides relative manipulation of dental casts hingedly and yieldingly through full orbital and masticatory ranges wherein every phase and condition of dental occlusive relationships can be accurately portrayed and duplicated. The inexpensive disposable articulator of present invention was made possible by the built-in design and novel features which eliminate many steps and manual operations, increasing both productivity and quality dramatically.

The articulator of the present invention consists of three parts—a lower frame, an upper frame, and a middle frame. The lower frame is comprised of an elongated rectangular box, a deformable bracket, and a snap-fit male hinge. The upper frame is comprised of an elongated, channeled surface, a deformable bracket, a snap-fit female hinge, and a platform with holes. The middle frame is in the shape of a picture frame, which is snap-seated on top of the elongated box in the lower frame.

The lower frame is for the master dental cast in which the teeth under restoration reside. The elongated box in the lower frame has an open bottom and an insert at the top. The outer surface of the insert bears a series of functional grooves. The imprints of the grooves are copied onto the bottom of the cast when the model stone is poured. With these imprints, the dies made out of the master cast can return to their original positions. In the middle of the platform at the front end of the lower frame is a hole to hold a plastic bar which adjusts the vertical height of the jaws.

The snap-fit hinge provides pivotal movement around a pivot axis. The hinge in the present invention is made of two components—a male and a female component. The two components are not mirror images of each other.

The upper frame is for mounting the opposing dental cast. The bottom (inner) surface of the upper frame is divided into two different areas. Along the middle of the frame is a flat area with a slotted opening. This flat area can be used to attach a pre-prepared cast with an adhesive. Outside of the flat area are two rectangular boxes, one on each side. These boxes are provided so that the model stone can be poured onto the surface to mount the opposing cast. Some of the poured stone enters the slotted opening and locks the cast onto the frame. The platform at the front end of the upper frame has three holes. With a plastic bar in place in one of the three holes, the upper and lower casts are maintained at the original vertical height of the jaws even when all of the patient's teeth are missing on the cast. The L-shaped deformable bracket supports the hinge assembly. The horizontal section of the bracket may be softened by heating for quick bite correction and remounting.

The middle frame is for removing any excess model stone and increasing the master model thickness by the height of the frame. When the middle frame is seated on top of the elongated box, a rectangular box is formed. A master cast is made and mounted when this rectangular box is filled with the model stone and the impression is placed on top of the box, with all spaces in between filled with stone.

By incorporating all of the above advantages in the design, the present invention yields superior model work with regards to quality, accuracy, workmanship and productivity. The imprinted grooves on the bottom of the master cast yield greater accuracy over the conventional grooves made with an instrument by hand. No prior art disposable articulators feature built-in vertical stops, nor do they have a built-in feature for quick remounting. No prior art disposable articulators have the versatility to accommodate any type of impression trays, whether the impressions are already poured or not. All of these features contribute to the quality of the present invention.

Important requirements of a disposable articulator include cost, productivity, quality, remountability, the presence of vertical stops, and versatility.

Accordingly, the primary objective of the present invention is to provide an improved disposable articulator.

Another objective of the present invention is to be able to accommodate all single-sided, double-sided, quadrant-arch, half-arch, or full-arch impression trays. It accommodates unpoured impression trays (wet) as well as poured casts (dry).

Yet another objective of the present invention is to provide an articulator with a means of correcting the mounting quickly.

Still another objective of the present invention is to incorporate a built-in vertical stop.

A further objective of the present invention is to provide a means of adjusting the vertical height.

Yet a further objective of the present invention is to reduce working time, therefore increasing productivity.

Still a further objective of the present invention is to provide an articulator with a self-cleaning mechanism which eliminates the need for model trimming and grinding, dramatically increasing productivity.

An additional objective of the present invention is to provide an articulator that yields accuracy of the crowns.

Another objective of the present invention is to yield quality workmanship and aesthetics.

Still another objective of the present invention is to provide an articulator which automatically puts grooves on the bottom of the master cast, eliminating the need for hand-grooving.

A further objective of the present invention is to provide an articulator which automatically exposes the pins.

Yet a further objective of the present invention is to provide an articulator with an improved method of assembling and disassembling dental models.

Still a further objective of the present invention is to provide an articulator which is simple, inexpensive and disposable.

BRIEF DESCRIPTION OF THE DRAWINGS

The features and advantages of the present invention may be observed with greater clarity in the following drawings, in which.

DETAILED DESCRIPTION OF THE PREFERRED EMBODIMENTS

As used herein, the term "occlusal movement" shall refer generally to movement of the model which brings the opposing surfaces of the teeth of the two jaws into contact from a spread-apart position, whereas the term "occlusion" refers to the position of the teeth when the opposing surfaces of the teeth are in contact with one another in proper position for bite registry. The term "masticatory movement" shall refer generally to a motion which is the combination of vertical, horizontal and/or side-to-side movement of the teeth and jaws such as occurs when chewing with at least a portion of the upper teeth in contact with at least a portion of the lower teeth.

Figure 1A:
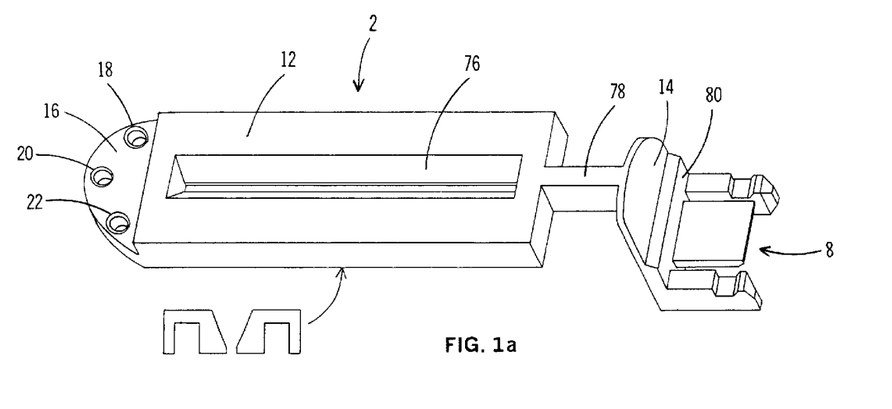
FIGS. 1a–1c are top views of sub-assemblies of a posterior articulator of the present invention.
Figure 1B:
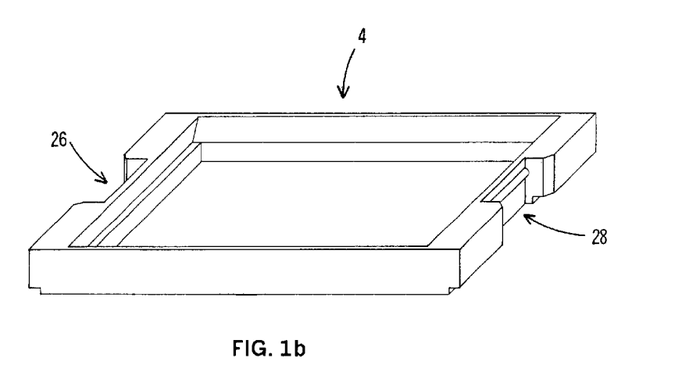
Figure 1C:
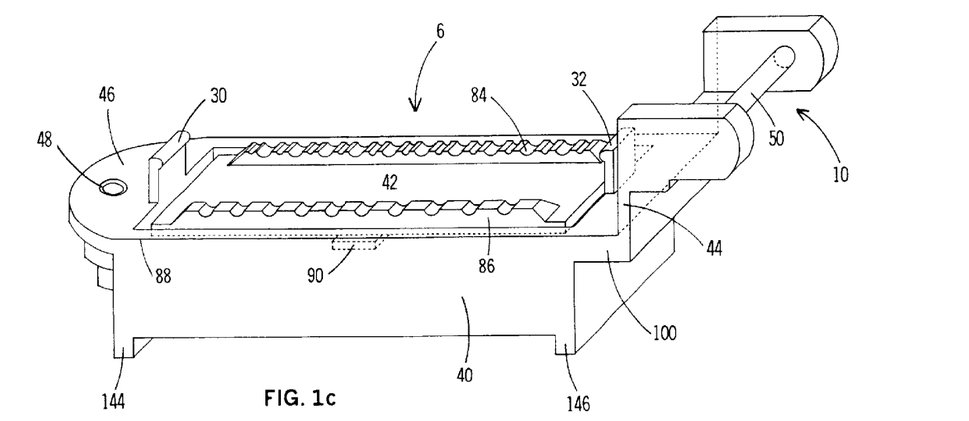

Referring jointly to FIGS. 1a, 1b, 1c, and FIG. 3a, the articulator of the present invention consists of three sub-assemblies—upper frame 2 (FIG. 1a), middle frame 4 (FIG. 1b), and lower frame 6, (FIG. 1c). The upper and lower frames (2,6) are interconnected by snap-fit hinges (8,10) which produce a pivotal movement around the pivot axis.

The upper frame 2 is comprised of an elongated channeled surface 12, a resiliently deformable bracket (78,14,80), a snap-fit female hinge assembly 8, and a platform 16 with holes (18,20,22). The upper frame 2 holds the opposing model 36 (FIG. 3d).

The middle frame 4 is a picture-frame shape and is snap-seated on top of the lower frame 6. The cutouts (26,28) at both ends mate with the retentive latches (30,32) of the lower frame 6. The impression tray 34 (FIG. 3b) is placed between the middle frame 4 and the upper frame 2 and all spaces therein are filled with model stone, forming the upper and lower casts (36,38) (FIG. 3f).

The lower frame 6 is comprised of an elongated box 40, a grooved insert 42, a resiliently deformable bracket 44, a snap-fit male hinge assembly 10, and a platform 46 with a hole 48. The lower frame 6 houses the master model 38 (FIG. 3d) on which the teeth under restoration reside.

Figure 3A:
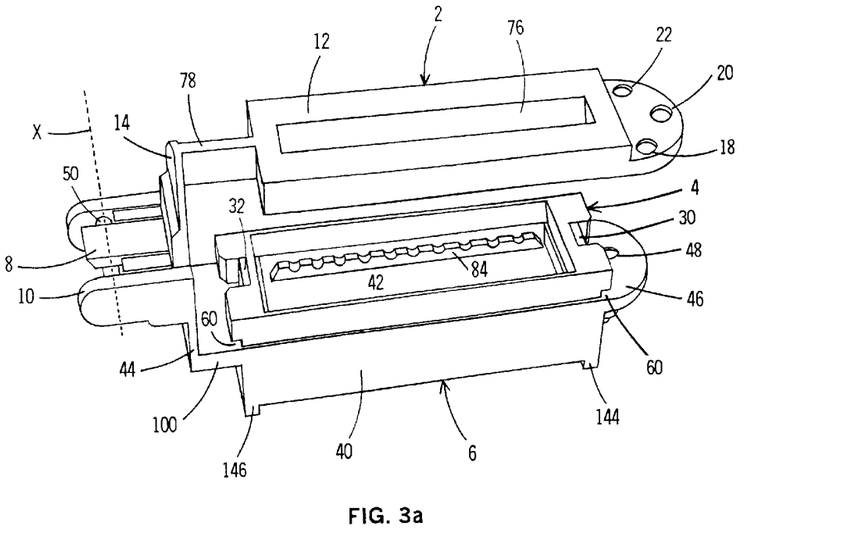
FIG. 3a is a side perspective view of a posterior articulator of the present invention for posterior teeth.
Figure 3B:
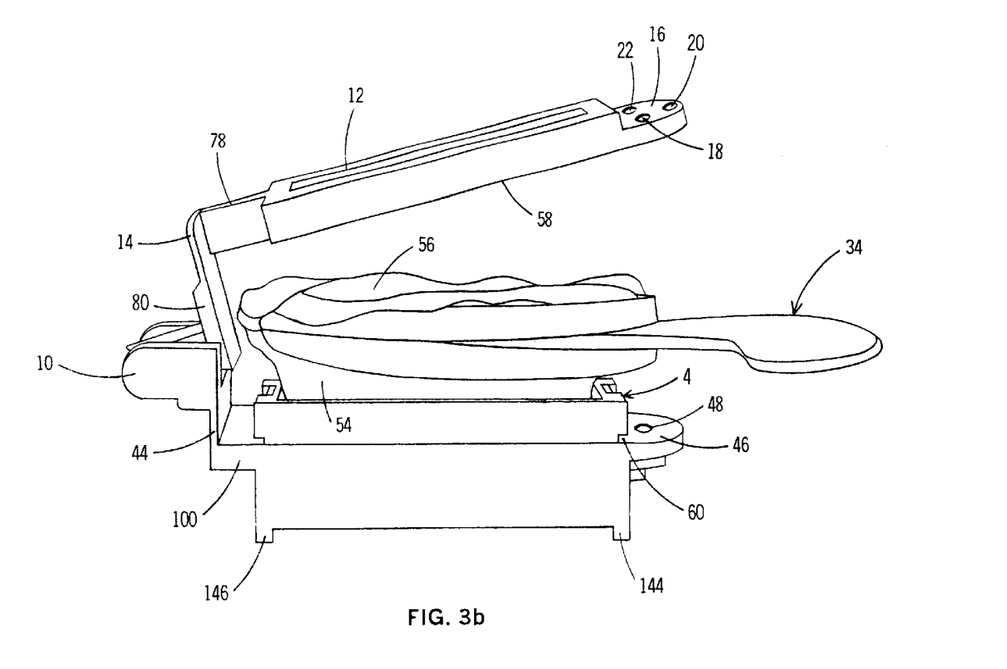
FIGS. 3b–3f are step-by-step pictures showing how to use the present invention.
Figure 3C:
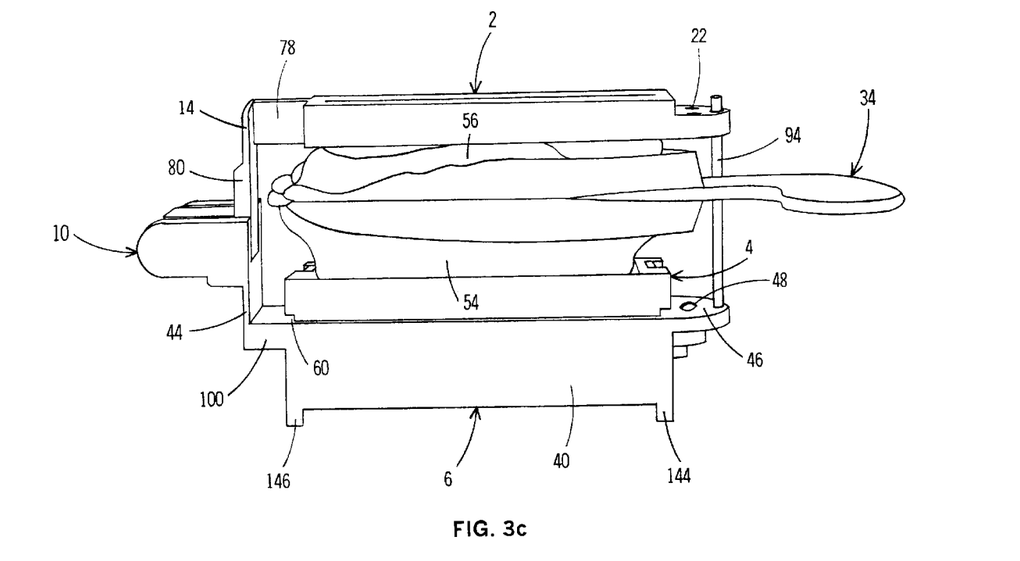
Figure 3D:
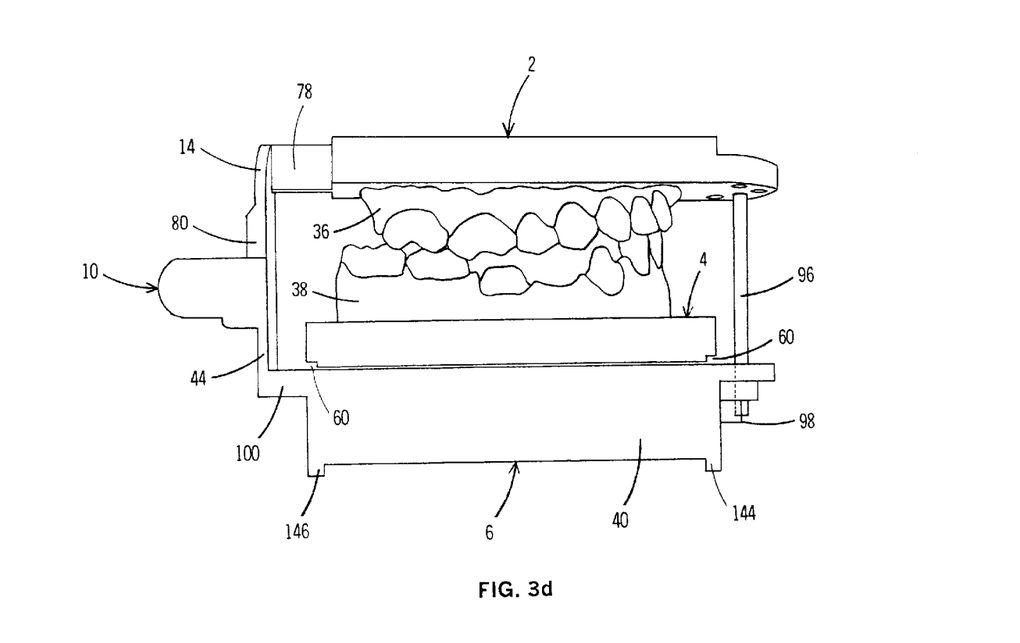
Figure 3E:
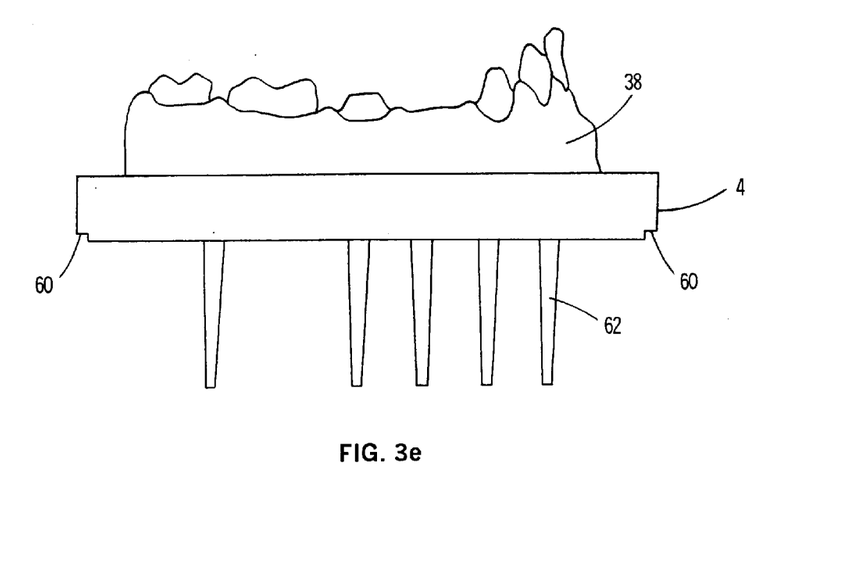
Figure 3F:
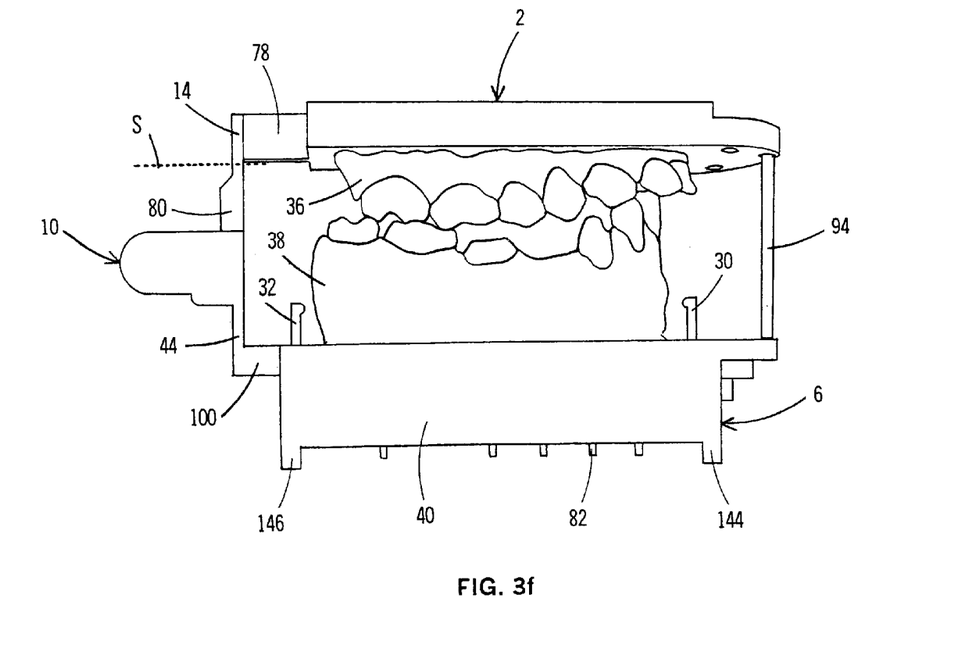

FIGS. 3a–3f are step-by-step procedures showing how to use the present invention. In FIG. 3a, an articulator is preassembled before the impression is poured with stone. The upper and lower frames are connected by their hinges by inserting the rod 50 on the male hinge assembly 10 on the lower frame 6 to the opening of the female hinge assembly 8 on the upper frame 2. The middle frame 4 is snap-seated on top of the lower frame 6 via two latches.

Referring to FIG. 3b, the model stone is mixed and poured into the middle frame 4. The master side 54 of the impression tray 34 is filled with the model stone and the impression tray 34 is placed on top of the middle frame 4. The master cast is formed and mounted. Some time is allowed for the stone to set.

It is noteworthy that, in the present invention, the master side 54 of the impression 34 is poured first. In some of the known prior art articulators, the opposing side 56 is poured first. Pouring the opposing side first is, strictly speaking, not technically acceptable. The stone expands when set even in small amounts, deforming the impression. The weight of the stone poured can also distort the impression on the master side, which has not yet been poured.

Referring to FIG. 3c, the model stone is mixed and poured onto the opposing side 56 of the impression 34. A small amount of model stone is spread over the inner side of the upper frame 2, and the upper frame 2 is closed. The opposing cast is formed and mounted now. Some time is allowed for the stone to set.

At this time, a plastic bar 94 may be placed in one of the three holes (18,20,22) to serve as a vertical stop.

Referring now to FIG. 3d, the impression tray is removed.

In FIG. 3e, the master model 38 surrounded by the middle frame 4 is removed from the lower frame 6 by lifting up the bottom ends 60 of the middle frame 4 with a flat-head screw driver. Necessary holes are made on the bottom surface of the master model 38 and pins 62 are placed with an adhesive. A separating medium is applied on the bottom surface of the master model 38 so that the stone poured upon it will not stick to the surface. The top insert 42 (FIG. 3a) of the lower frame 6 is detached by pressing one end of the insert 42 with the fingers. The pinned master model 38, still surrounded by the middle frame 4, is returned to the top of the lower frame 6. The top side of the elongated box 40 (FIG. 3a) of the lower frame 6 is now sealed by the master cast and the middle frame 4.

Figure 2A:
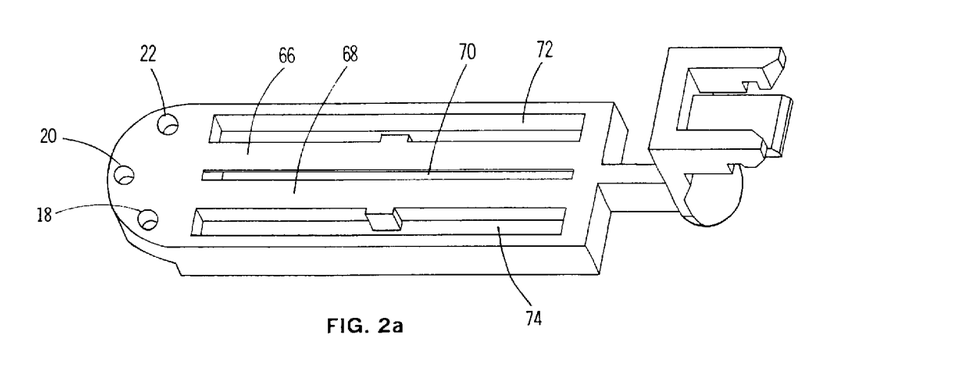
FIGS. 2a–2c are bottom views of sub-assemblies of a posterior articulator of the present invention.
Figure 2B:
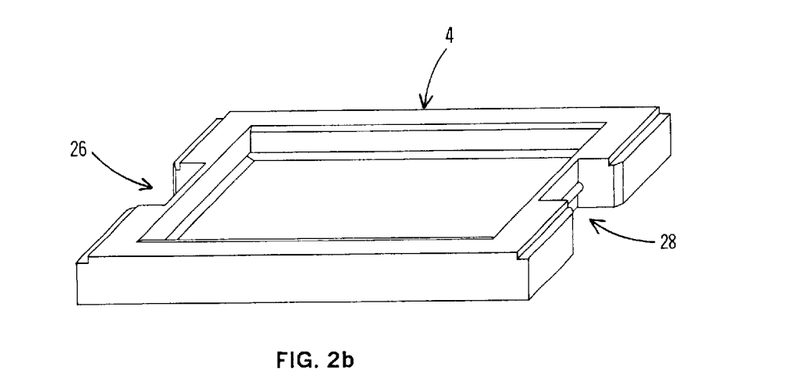
Figure 2C:
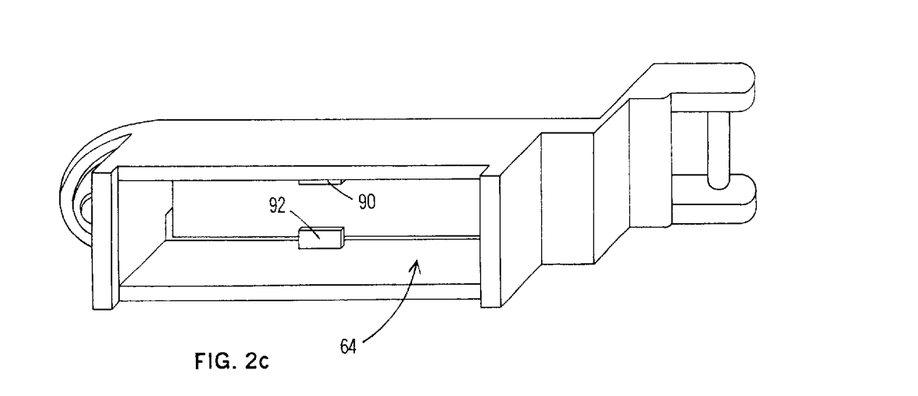

In FIG. 3f, to form a base for the pinned master cast 38, the stone mix is poured into the lower frame box 40 from the open-bottom side 64 (FIG. 2c).

Now the impression 34 has been poured and mounted. The upper and lower models (36,38) are formed and hinged together. The master model 38 on the lower frame 6 can be further prepared for die work. The mounted casts (36,38) may now be used to fabricate and evaluate the crown under a realistically simulated environment for occlusal and masticatory movements of the mouth. The fit of the crown is evaluated as well as whether the crown is in occlusion or interferes with occlusion.

FIG. 1a shows an upper frame 2 of the half-arch articulator of the present invention. The major components of the frame are an elongated channeled rectangular surface 12, a platform 16 with three holes (18,20,22), a flexible bracket (78,14,80), and a female hinge assembly 8.

FIG. 2a shows the inner surface of the upper frame 2, which provides two distinctive geometrical areas—flat rectangular areas (66,68) with an open slot 70 in the middle, and an area containing two rectangular boxes (72,74). The flat rectangular areas (66,68) in the middle are provided to attach a pre-prepared opposing cast with an adhesive. The open slot 70 in the middle of the frame allows the application of an accelerator to accelerate setting of the adhesive. Two rectangular boxes (72,74) receive the model stone when the impression is poured in the articulator. The size of the rectangular boxes (72,74) is large enough to hold excess stone, preventing overflow, and thereby eliminating the conventional need for model-cleaning and trimming work.

Referring to FIG. 1a, the outer surface of the upper frame 2 provides an open slot 76 of a V-shape. When the model stone is poured along the open slot from the other side, some of the stone flows into the slot 76. Since the slot is V-shape, the stone locks the model in place when set.

The platform 16 attached at the front end of the upper frame 2 has holes (18,20,22) at the far left, far right, and middle of the frame. After the pouring of the impression and before removing the impression tray 34 (FIG. 3c), a plastic bar 94 can be dropped through one of the three holes (18,20,22) until it reaches the platform 46 of the lower frame 6. At this time, the adhesive can be applied to the hole to hold the plastic bar 94 firmly in place. Now the plastic bar 94 serves as a vertical height maintainer (or a vertical stop).

An angled bracket (78,14,80) is attached at the rear end of the frame. The horizontal section 78 of the bracket (78,14,80) is used to support the upper frame 2 at it's level and to correct the mounting of the upper and lower models. The horizontal section 78 of the bracket (78,14,80) can be heated with a heat source, such as a flame or a soldering iron, as the melting point of the material is somewhat low. When the bracket 78 melts, the upper frame 2 is free to move about and the correct bite relationship can be found. At this time the heated section can be cooled and hardened to complete the remounting process. This process can be repeated as many times as necessary. The vertical section (14,80) of the bracket (78,14,80) is made in two thicknesses. The lower portion 80 of the vertical section (14,80) of the bracket (78,14,80) is made substantially thick so that the heat is absorbed, protecting the hinge assembly 8 from heat. The top portion 14 of the vertical section (14,80) of the bracket (78,14,80) is made substantially thin so that it can flex resiliently and yieldingly resist the external forces applied thereon. This feature enables the articulator to simulate realistic occlusal and masticatory movements of the mouth. Translational movement in any plane is effected by the flexing bracket (78,14,80). Pivotal movement of the casts is effected by the hinge line X (FIG. 3a).

A female hinge assembly 8 is provided at the end of the bracket 80. The female hinge assembly 8 mates with the male hinge assembly 10 of the lower frame 6 for rotation about pivot axis X (FIG. 3a). The mating is accomplished by inserting the male hinge rod 50 into the opening of the female hinge assembly 8.

Figure 4:
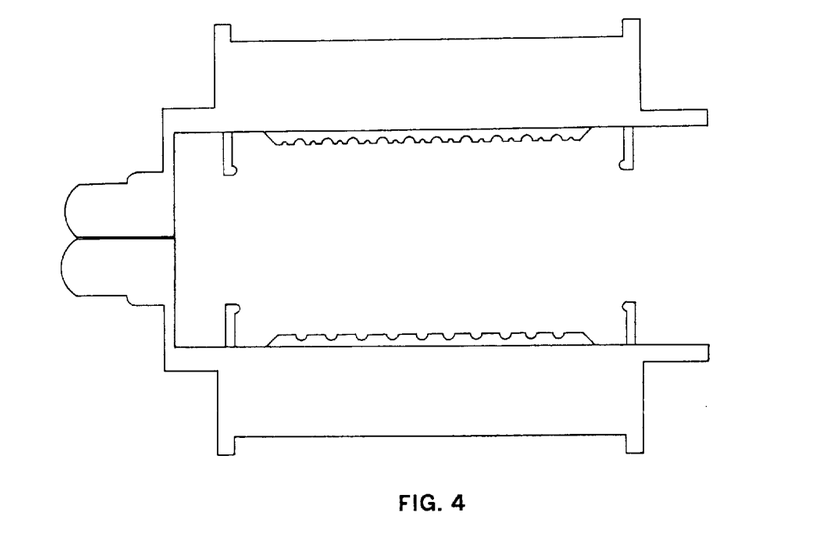
FIG. 4 is a side view of a back-to-back articulator, which is used when the crowns under fabrication are on both upper and lower jaws.

When the crowns under construction are on both upper and lower jaws, a back-to-back articulator as shown in FIG. 4 is required. This back-to-back articulator can be assembled by switching the upper frame 2 with the lower frame 6 (FIG. 3f). This is accomplished by sawing off the upper frame 2 across at the top end of the vertical section (14,80) of the bracket as indicated by line S (FIG. 3f), placing a lower frame 6 upside down over the cut section of the bracket, and then fixing with an adhesive.

Referring to FIGS. 1b and 3a, the middle frame 4 is snap-seated on top of the lower frame 6. At both ends of the frame are rectangular cutouts (26,28) made to fit into two retentive latches (30,32) on the lower frame 6. The inner dimensions of the middle frame 4 are equal to the dimensions of the insert 42 on the lower frame 6, hence, when seated, a rectangular box is formed. When pouring the impression, this box is filled with the model stone and the impression is placed on top of the box, with all spaces in between filled with stone. The width of the middle frame 4 is equal to that of the lower frame 6. Therefore, when the middle frame 4 is seated on top of the lower frame 6, the top side of the lower frame 6 becomes completely sealed.

The middle frame 4 serves two important functions. It serves as a cleaning device and guarantees minimum die thickness. Upon completion of the model work, the middle frame 4 is removed and discarded. The removal of the middle frame 4 breaks off and removes all excess stone, making it unnecessary to trim the cast on a model trimmer or grind off excess stone. As a guarantee of die thickness, the height of the frame becomes an added thickness to the cast. This feature is important, especially when the depth of the impression is very shallow. If a shallow impression is poured on a flat surface without the middle frame 4, the cast will become so thin that it may result in accidental breakage or become difficult to work with.

FIG. 1c shows a lower frame 6 of the half-arch articulator of the present invention. The main elements of the frame are an elongated box 40, a grooved insert 42, two retentive latches (30,32), a platform 46 with a hole 48, a resiliently deformable bracket (44,100), and a male hinge assembly 10.

The elongated box 40 in the lower frame 6 has an open bottom 64 (FIG. 2c) and a detachable top 42. The length of the elongated box 40 is that of a typical impression tray. The depth at the middle of the box is slightly less than the length of the pins 62 (FIG. 3e) commonly used in the industry. This embodiment allows for the tips 82 (FIG. 3f) of the pins 62 to be exposed when the model stone is poured into the box. This embodiment eliminates the need to dig up the stone with an instrument to expose the pins. The height of the front and rear sides (144,146) of the box 40 are slightly longer than the pins 62 so that when the articulator is on the work bench, the pins 62 are secured from the work surface.

The top surface of the insert 42 of the elongated box 40 bears a grooved pattern (84,86) which is imprinted on the bottom of the cast when the model stone is poured onto it. With these imprints, dies (cut sections of the master cast) can be brought to their original position, and dies can remain seated stable. The two rows of the grooved patterns (84,86) on both sides of the insert 42 are different to help find the orientation of the dies. The top insert 42 is raised slightly higher than the rim 88 (FIG. 1c) of the elongated box 40 and the dimensions of the insert 42 are same as the inner dimensions of the middle frame 4. This embodiment permits the middle frame 4 to be seated around the insert 42 in a wrapping fashion, forming a rectangular box into which the model stone can be poured. The rectangular box serves as a mold, producing uniquely sized casts for consistent quality and accuracy. By use of the insert 42 with grooved patterns (84,86), the need to make grooves by hand is eliminated. The insert 42 is held to the elongated box 40 by two connecting points (90,92) (FIG. 2c) located at the middle of the insert 42. This insert 42 is detached from the elongated box 40 by depressing one end of the insert 42 with the fingers.

Two retentive latches (30,32) are provided for the middle frame 4 to be firmly seated around the top insert 42 on top of the elongated box 40.

The front end of the elongated box 40 bears a platform 46 with a hole 48. The platform 46 serves as a stop for the plastic bar 94 (FIG. 3c) placed on the upper frame 2. The plastic bar 94 maintains the vertical distance of the upper and lower models, whether or not there are any teeth on the casts. The hole 48 on the platform 46 can hold a plastic bar 96 (FIG. 3d) which serves as a vertical height adjuster. The ability to adjust the vertical height is useful during the porcelain build-up process in a dental laboratory. (Porcelain build-up is the process of stacking porcelain onto a crown under fabrication.) The porcelain materials shrink when baked. The shrinkage needs to be compensated by stacking on more porcelain. When technicians build a crown with porcelain, they build it larger than the desired size of the crown to compensate for the shrinkage. To accomplish this, a plastic bar 96 can be placed in the hole 48 to increase the vertical height, after which the porcelain can be built up until it reaches the opposing teeth. To make it easy to install a plastic bar 96 in the hole 48, the diameter of the hole 48 is slightly larger than the commonly used gauge 8 plastic bar, and the hole 48 is deep enough to hold the plastic bar 96 in place. The bottom 98 (FIG. 3d) of the hole 48 is half open so that any debris can be removed or allowed to fall off.

An angled bracket (44,100) is attached to the rear wall of the elongated box 40. The horizontal section 100 of the bracket (44,100) is made thick and solid to prevent any deforming. However, the vertical section 44 of the bracket (44,100) is made thin so that it is flexible and can yieldingly resist external forces applied thereon. By a combination of the flexing bracket and pivotal movement of the hinge assemblies (8,10), the full range of occlusal and masticatory movements can be simulated.

A male hinge assembly 10 is provided at the end of the bracket 44. The male hinge assembly 10 mates with the female hinge assembly 8 on the upper frame 2 for hinged rotation relative to one another. The mating is accomplished by inserting the rod 50 in the male hinge assembly 10 into the opening of the female hinge assembly 8 on the upper frame 2. The hinge in the present invention is made in two different parts—the male part 10 and the female part 8. They are not mirror images of one other.

Figure 5:
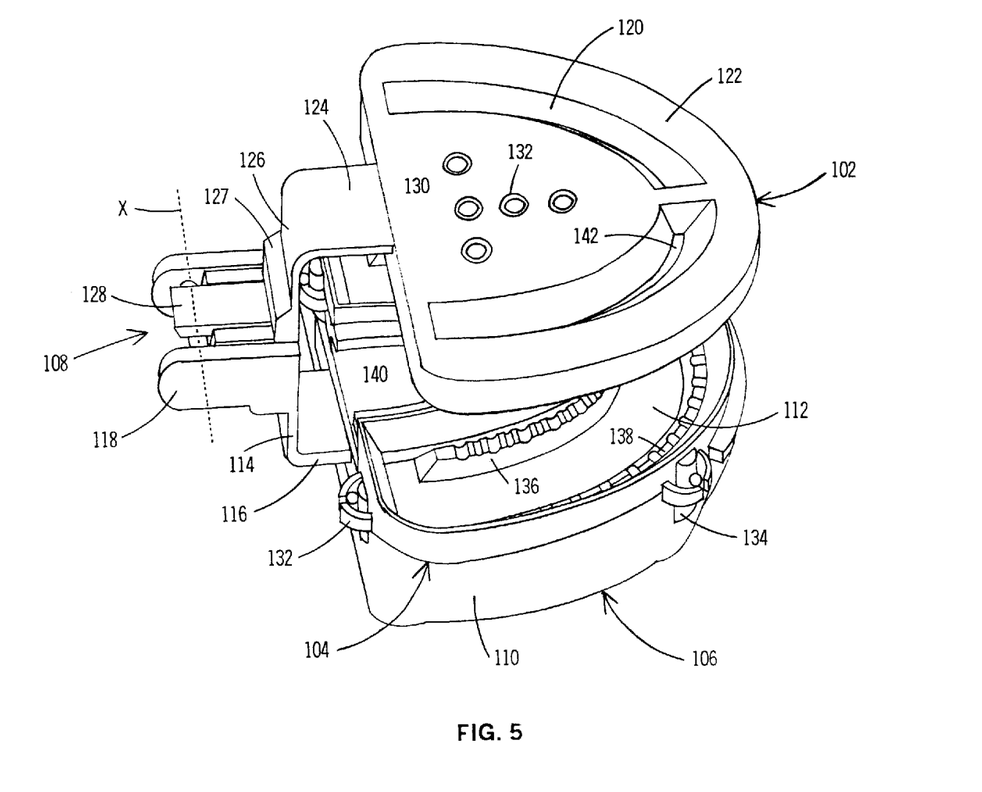
FIG. 5 is a side perspective view of the full-arch articulator of the present invention for anterior or full-arch teeth.

FIG. 5 shows a full-arch articulator of the present invention. The articulator consists of three parts—the lower frame 106, upper frame 102, and middle frame 104. The upper frame 102 and the lower frame 106 are interconnected by snap-fit hinge assemblies 108 which produce a pivotal movement around a pivot axis X.

The lower frame 106 is comprised of a full-arch box 110, a grooved insert 112, a resiliently deformable bracket (114, 116), and a snap-fit male hinge assembly 118. The lower frame 106 houses the master model on which the teeth under restoration reside.

The upper frame 102 is comprised of a channeled 120 full-arch surface 122, a resiliently deformable bracket (124, 126,127), a snap-fit female hinge assembly 128, and a platform 130 with holes 132. The upper frame 102 holds the opposing model.

The full-arch box 110 in the lower frame 106 has an open bottom and a detachable top insert 112. The size of the full-arch box 110 is that of a typical impression tray.

The top surface of the insert 112 of the full-arch box 110 bears two rows of grooved patterns (136,138) which are imprinted on the bottom of the cast when the model stone is poured onto it. With these imprints, dies (cut sections of the master cast) can be brought to their original positions, and dies can remain seated stably. The top insert 112 is raised slightly higher than the rim of the full-arch box 110 and the dimensions of the insert 112 is same as the inner dimensions of the middle frame 104. This embodiment permits the middle frame 104 to be seated around the insert 112 in a wrapping fashion, forming a top full-arch box (104,112) into which the model stone can be poured. The top full-arch box (104,112) serves as a mold, producing uniquely sized casts with consistent quality and accuracy. By use of the insert 112 with grooved patterns (136,138), the need to make grooves by hand is eliminated. The insert 112 is held to the full-arch box 110 by four connecting points and made detachable from the full-arch box 110 by depressing the front end of the insert 112 with the fingers.

Around the full-arch box 110, four male latches 134 are provided for the middle frame 104 to be firmly seated around the insert 112.

The flat surface 140 in the middle of the full-arch box 110 serves as a stop for the plastic bar placed in the hole at the upper frame 102. The plastic bar maintains the vertical distance of the upper and lower models, whether or not there are any teeth on the casts.

An angled bracket (114,116) is attached to the rear of the full-arch box 110. The horizontal section 116 of the bracket (114,116) attached to the full-arch box 110 is made thick and solid for firm support. The vertical section 114 of the bracket (114,116) is made thin so that it is flexible and can yieldingly resist external forces applied thereon. By a combination of the flexing bracket and pivotal movement of the hinge, the full range of occlusal and masticatory movements can be simulated.

A male hinge assembly 118 is provided at the end of the bracket 114. The male hinge assembly 118 mates with the female hinge assembly 128 on the upper frame 102 for hinged rotation relative to one another about pivot axis X. The hinge assembly in the present invention is made in two different parts—one is the male part and the other is the female part. They are not mirror images of one other.

The inner surface of the upper frame 102 provides two distinctive geometrical areas—a flat horse-shoe shaped surface with an open slot in the middle and an area containing two horse-shoe shaped boxes. The flat horse-shoe shaped surface in the middle is provided to attach a pre-prepared opposing cast with an adhesive. The open slot 142 in the middle of the frame facilitates the usage of an accelerator to accelerate setting of the adhesive.

The outer surface 122 of the upper frame 102 provides an open slot 142 of a V-shape. When the model stone is poured along the open slot from the other side, some of the stone flows into the slot. Since the slot is V-shaped; the stone locks the model in place when set.

Five holes 132 are provided in the middle of the upper frame 102. A plastic bar can be dropped through one of the five holes 132 until it reaches the platform 140 of the lower frame 106. At this time the adhesive can be applied to the hole to hold the plastic bar in place firmly. Now the plastic bar serves as a vertical height maintainer (or a vertical stop). Multiple plastic bars may be installed to achieve balance.

An angled bracket (124,126,127) is attached at the rear end of the frame. The horizontal section 124 of the bracket (124,126,127) is used to support the upper frame 102 at it's level and to correct the mounting of the upper and lower models. The horizontal section 124 of the bracket (124,126,127) can be heated with a heat source, such as a flame or a soldering iron, as the melting point of the material is somewhat low. When the bracket melts, the upper frame 102 is free to move about and the correct bite relationship can be found. At this time the heated section can be cooled and hardened to complete the remounting process. This process can be repeated as many times as necessary. The vertical section (126,127) of the bracket (124,126,127) is made in two thicknesses. The lower portion 127 of the vertical section of the bracket (124,126,127) is made substantially thick so that the heat is absorbed, protecting the hinge assembly 128. The top portion 126 of the vertical section of the bracket (124,126,127) is made substantially thin so that it can flex resiliently and yieldingly resist the external forces applied thereon. This feature enables the articulator to realistically simulate the occlusal and masticatory movements of the mouth. Translational movement in any plane is effected by the flexing bracket (124,126,127). Pivotal movement of the casts is effected by the hinge line X.

A female hinge assembly 128 is provided at the end of the bracket 127. The female hinge assembly 128 mates with the male hinge assembly 118 of the lower frame 106 for rotation about pivot axis X.

The middle frame 104 is snap-seated on top of the lower frame 106. Four retentive circular arms 132 on the middle frame 104 mate with four latches 134 on the lower frame 106. The inner dimensions of the middle frame 104 are equal to the dimensions of the insert 112 on the lower frame 106, hence, when seated, a full-arch box is formed. When pouring the impression, this box is filled with the model stone and the impression is placed on top of the box, with all spaces in between filled with stone. The width of the middle frame 104 is equal to that of the lower frame 106. Therefore, when the middle frame 104 is seated on top of the lower frame 106, the top side of the lower frame 106 becomes completely sealed.

The middle frame 104 serves two important functions. It serves as a cleaning device and guarantees minimum die thickness. Upon completion of the model work, the middle frame 104 is removed and discarded. The removal of the middle frame 104 breaks off and removes all excess stone, making it unnecessary to trim the cast on a model trimmer or grind off excess stone. As a guarantee of die thickness, the height of the frame becomes an added thickness to the cast. This feature is important, especially when the depth of the impression is very shallow. If a shallow impression is poured on a flat surface without the middle frame 104, the cast will become so thin that it may result in accidental breakage or become difficult to work with.

When the crowns under construction are on both upper and lower jaws, a back-to-back articulator is required. This back-to-back articulator can be assembled by switching the upper frame 102 with the lower frame 106. This is accomplished by sawing off the upper frame 102 across at the top end of the vertical section 126 of the bracket (124,126,127), placing a lower frame 106 upside down over the cut section of the bracket (124,126,127), and then fixing with an adhesive.

While a particular construction of the present invention is illustrated and described, the construction is subject to modifications, substitutions and rearrangements without departing from the spirit and scope of the invention. It is, therefore, not desired to restrict the invention to the particular form of construction illustrated and described, but to cover all modifications, substitutions and rearrangements that may fall within the spirit and scope of the present invention, as set forth in the appended claims.

What is claimed is:

1. An articulator for correlating the upper and lower dental casts corresponding to the upper and lower sets of a patient's teeth in a desired occlusal relationship for the simulation of occlusal and masticatory movements by application of force to the dental casts, the said articulator comprising:

(a) a lower frame comprising a box with an open bottom;

(b) a top insert detachably supported on the lower frame;

(c) a platform extending from one end of the lower frame;

(d) an L-shaped resiliently deformable bracket extending from the opposite end of the lower frame and incorporating a male hinge assembly for interconnecting said male hinge assembly with an opposing female hinge assembly;

(e) an upper frame having upper and lower surfaces and having a flat channeled surface provided with an elongated open slot in the middle of the top surface and rectangular boxes along the flat channeled lower surface parallel with and on opposite sides of said open slot;

(f) a resiliently deformable bracket extending from one end of said upper frame;

(g) a platform with holes extending from the opposite end of said upper frame;

(h) a female hinge assembly on the other end of said upper frame extending in a direction opposite said platform;

(i) a middle frame having inner and outer peripheries, the inner peripheral dimensions of said middle frame matching those of said detachable top insert supported on the lower frame so that said frame fits around said detachable top insert for sealing the top of the box in the lower frame, the top border of said frame being knife-edged to facilitate a cutting effect;

(j) retentive latches on said middle and lower frames; and (k) undercut edges formed in the lower edge of said middle frame adapted to receive a pry tool to selectively lift and separate the middle frame from the lower frame.

2. The articulator of claim 1, wherein the detachable top insert supported on the lower frame is provided with a series of grooves adjacent opposite peripheral edges of said top insert at an elevated level wherein the patterns of said series of grooves are impressed into the bottom of the cast when the model stone is poured and allowed to harden.

3. The articulator of claim 2, wherein pins are secured to the bottom of the cast to project downwardly therefrom through said lower frame and the depth of the box in the lower frame is slightly more shallow than the length of the pins thereby exposing the distal end portions of the pins, and means on the underside of said lower frame projecting below the distal end portions of the pins whereby when the articulator is supported on a work bench the pins are spaced from the work bench.

4. The articulator of claim 1, wherein said hole centrally disposed in said platform at said one end of the lower frame is of predetermined diameter and depth, and a support bar is fixed in said hole and extends between said upper and lower frames to support said frames in a predetermined orientation.

5. The articulator of claim 1, wherein said male hinge assembly includes a rod extending transverse to said upper frame and forms a pivotal axis enabling selective relative pivotal displacement of said upper and lower frames.

6. The articulator of claim 1, wherein the outer surface of the upper frame provides a V-shaped slot with an open bottom so that some of the stone flows into the slot to lock the model in place when the stone sets.

7. The articulator of claim 1, wherein the platform at the one end of the upper frame of the articulator is provided with holes at the far left, the far right and middle of the platform, and a support bar fixed to said upper frame extends through one of the holes and impinges on the platform of the lower frame to serve as a vertical height gauge between said upper and lower frames.

8. The articulator of claim 1, wherein an angled bracket having a horizontal portion selectively softenable by application of heat is fixed to the end of the upper frame remote from said platform to normally support the upper frame at a predetermined level in relation to the lower frame, whereby upon the application of heat to said horizontal portion of the bracket it is softened so that the upper frame may be moved around to simulate the occlusal and masticatory movements of the teeth to correct the bite relationship between sets of teeth supported between said upper and lower frames, then allowed to cool and harden to complete the remounting process.

9. The articulator of claim 1, wherein removal of the middle frame upon completion of the model work by lifting the middle frame from to separate it from the lower frame breaks off and removes all excess stone to produce a master cast of adequate thickness.

10. The method of casting dental impressions in stone and mounting said dental casts in an articulator to correlate the casts throughout a full range of occlusal and masticatory movement, said method consisting of the sequential steps of:

(a) assembling an articulator by pivotally joining an upper frame to a lower frame in vertically spaced relation and seating a middle frame on top of the lower frame spaced from the upper frame;

(b) mixing the model stone and pouring the stone into the frame and the master side of the impression and then closing the articulator and allowing the cast stone to harden, whereupon the articulator is opened;

(c) mixing the model stone and pouring the stone into the opposing side of the impression and the inner side of the upper frame, closing the articulator and allowing the cast stone to harden, whereupon the articulator is opened;

(d) removing the impression tray from the opened articulator;

(e) removing the middle frame and the master cast together from the lower frame by lifting the bottom ends of the middle frame;

(f) forming holes in the bottom surface of the master cast and selectively securing pins therein;

(g) applying a separating medium on the bottom of the master cast and the lower frame;

(h) returning the middle frame and the master cast together to their original positions on the lower frame; and (i) mixing the model stone and applying the stone to fill the lower frame and applying stone to the underside of the master cast to form a unitary casting.

* * * * *